United States Patent
Tour et al.

(10) Patent No.: US 7,625,988 B2
(45) Date of Patent: Dec. 1, 2009

(54) FLAME RETARDANT POLYMERS HAVING PENDANT GROUPS RELATED TO BISPHENOL-C AND MONOMERS FOR SYNTHESIS THEREOF

(75) Inventors: James M. Tour, Bellaire, TX (US); Joshua L. Jurs, Houston, TX (US); Jason J. Stephenson, Humble, TX (US)

(73) Assignee: William Marsh Rice University, Houston, TX (US)

( * ) Notice: Subject to any disclaimer, the term of this patent is extended or adjusted under 35 U.S.C. 154(b) by 723 days.

(21) Appl. No.: 10/560,291

(22) PCT Filed: Jun. 18, 2004

(86) PCT No.: PCT/US2004/019414
§ 371 (c)(1),
(2), (4) Date: Dec. 12, 2005

(87) PCT Pub. No.: WO2004/113265
PCT Pub. Date: Dec. 29, 2004

(65) Prior Publication Data
US 2006/0178462 A1 Aug. 10, 2006

Related U.S. Application Data

(60) Provisional application No. 60/480,349, filed on Jun. 20, 2003.

(51) Int. Cl.
*C08F 12/00* (2006.01)
*C08F 18/00* (2006.01)
*C08F 18/20* (2006.01)

(52) U.S. Cl. .................. 526/292.5; 252/609; 526/242; 526/273; 526/291; 526/292.1; 526/292.7; 526/292.9; 526/293; 526/294; 526/295; 526/296; 526/298; 526/299; 526/304; 526/305; 526/307.5; 526/312; 526/313; 526/326; 526/328; 526/334; 528/369; 528/397; 528/402; 528/422; 560/20; 560/43; 560/157; 570/147; 570/182; 570/183; 570/184; 570/226; 585/400; 585/435

(58) Field of Classification Search ................ 526/242, 526/291, 292.1, 292.5, 292.7, 293, 294, 273, 526/292.9, 295, 296, 298, 299, 304, 305, 526/307.5, 312, 313, 326, 328, 334; 252/609; 528/369, 397, 402, 422; 560/20, 43, 157; 570/147, 182, 183, 184, 226; 585/400, 435
See application file for complete search history.

(56) References Cited

U.S. PATENT DOCUMENTS 3,225,106 A * 12/1965 Rabinowitz ................. 570/144

(Continued)

OTHER PUBLICATIONS

U.S. Appl. No. 60/480,349, filed Jun. 2003, Tour et al.*

(Continued)

*Primary Examiner*—Vasu Jagannathan
*Assistant Examiner*—Richard A Huhn
(74) *Attorney, Agent, or Firm*—Winstead PC

(57) ABSTRACT

The present invention is directed to novel flame retardant monomers and polymers, wherein the flame retardant properties of the polymers are provided by functionality in pendant groups attached to a polymer backbone (as opposed to the polymer backbone itself possessing flame retardant properties. The present invention is also directed to methods of making such polymers and monomers, and articles of manufacture incorporating such monomers and polymers.

14 Claims, 6 Drawing Sheets

U.S. PATENT DOCUMENTS

| | | | | | |
|---|---|---|---|---|---|
| 3,350,352 | A | * | 10/1967 | Smith et al. | 528/102 |
| 3,472,806 | A | * | 10/1969 | Hoyt et al. | 524/1 |
| 3,944,521 | A | * | 3/1976 | Bradley et al. | 526/204 |
| 4,049,726 | A | * | 9/1977 | Oosterwijk et al. | 570/182 |
| 4,148,841 | A | * | 4/1979 | Schwartz et al. | 523/515 |
| 4,274,998 | A | * | 6/1981 | Yamashita et al. | 524/288 |
| 4,982,007 | A | * | 1/1991 | Shimizu et al. | 568/429 |
| 5,248,752 | A | * | 9/1993 | Argyropoulos et al. | 528/49 |
| 6,875,895 | B2 | * | 4/2005 | Ueoka et al. | 568/633 |
| 2008/0058458 | A1 | * | 3/2008 | Harkins et al. | 524/464 |
| 2008/0221230 | A1 | * | 9/2008 | Hanson et al. | 521/80 |

OTHER PUBLICATIONS

"Vinyl bisphenol C for flame retardant polymers", Stephenson, Jason J.; Jurs, Joshua L.; Tour, James M. In SAMPE Conference Proceedings, Long Beach, CA, May 16-20, 2004, pp. 530-534.*

International Plastics Flammability Handbook, 2nd edition, Jurgen Troitzsch, p. 45.

J.R. Stewart, "Synthesis and Characterization of Chlorinated Bisphenol-Based Polymers and Polycarbodiimides as Inherently Fire-Safe Polymers," University of Massachusetts: Ahmerst, Massachusetts, (2000).

Jurs, et al., "Novel Flame Retardant Polymer Blends", SAMPE International Symposium, (2000), p. 1244-1248.

Lyon, R., In International Aircraft Fire and Cabin Safety Research Conference; Atlantic City, New Jersey, (2001).

Jurs, et al., "Novel flame retardant polyarylethers: synthesis and testing," 44 Polymer (2003), pp. 3709-3714.

Zhang, et al., "Thermal decomposition and flammability of fire-resistant, UV/visible-sensitive polyarylates . . ." 43 Polymer (2002), p. 5463-5472.

Furstner, "Olefin Metathesis and Beyond", 39 Angew. Chem. Int. Ed., (2000), pp. 3012-3043.

Stoliarov, et al., "Mechanism of the thermal decomposition of bisphenol C Polycarbonate; nature of its fire resistance", 44 Polymer (2003), pp. 5469-5475.

Factor, et al., "Polycarbonates from 1,1-dichloro-2, 2-bis(4-hydroxyphenyl)ethylene and bisphenol A: A Highly flame-resistant family, of engineering thermoplastics", 18 J. Polymer Sci.(1980), pp. 579-592.

Beasley, et al., "Development of a Panel of Immunoassays for Monitoring DDT . . . ", 46(8) J. Agric. & Food Chem (1998), pp. 3339-3352.

Horn, "Acrylic Resins", 2nd Ed., Reinhold Publishing Corp., NY (1962).

Wootton et al., "Physicochemical-Activity Relationships in Asymmetrical Analogues of Methoxychlor", 19 J. Med. Chem. (1976), pp. 1239-1247.

Hubacher, "Bis(p-hydroxyphenyl)acetic Acid", 24 J. Org. Chem. (1959), pp. 1949-1951.

* cited by examiner

A)

B)

FLAME RETARDANT POLYMERS HAVING PENDANT GROUPS RELATED TO BISPHENOL-C AND MONOMERS FOR SYNTHESIS THEREOF

CROSS REFERENCE TO RELATED APPLICATIONS

This Application claims priority to U.S. Provisional Patent Application Ser. No. 60/480,349 filed Jun. 20, 2003.

This invention was made with support from the Federal Aviation Administration, Grant Number 02-G-023.

FIELD OF THE INVENTION

The present invention relates generally to flame retardant materials, and more specifically to polymeric species and precursors comprising flame retardant functionality in pendant groups attached to a polymer backbone.

BACKGROUND

Polymer (plastic) materials have found their way into virtually every manufacturing sector. The ubiquity and abundance of these materials requires careful attention be paid to their flammability properties, especially for applications involving transportation, building materials, consumer goods, and electronics. As most polymeric materials are inherently flammable in their native state, additives are typically blended into polymeric materials to reduce their flammability.

Brominated organic compounds are commonly used as additives for retarding and slowing the flammability of plastic compounds they are blended with. They may be blended alone or in combination with other brominated or non-brominated flame retardants in a synergistic manner. Optionally, additional compounds may be added to the blend in order to achieve good flame-retarding results and maintain durability. In general brominated aliphatic compounds are more effective flame retardants than brominated aromatic compounds since they tend to break down more easily [International Plastics Flammability Handbook, $2^{nd}$ edition, Jurgen Troitzsch, p. 45]. However, brominated aromatic compounds are often more stable than the aliphatic bromides, therefore they discolor less readily.

A flame-retardant widely used in polyolefins and other plastics is tetrabromobisphenol A [International Plastics Flammability Handbook, $2^{nd}$ edition, Jurgen Troitzsch, p. 56] but it suffers from heavy blooming and has limited UV (ultraviolet radiation) stability. By "blooming" it is meant that a separation of the additive from the polymer matrix occurs, which has a negative effect on the surface appearance of the plastic articles. Many of the above mentioned flame-retardants require the additional use of a synergist such as antimony oxide, or else their activity as flame retardants is greatly diminished.

Bisphenol C (BPC) (1,1-dichloro-2,2-bis(4-hydroxyphenyl)ethylene) has been shown by many research groups to serve as a flame retardant and blendable additive as well as a monomer for producing flame retardant polymer materials [J. R. Stewart, "Synthesis and Characterization of Chlorinated Bisphenol-Based Polymers and Polycarbodiimides as Inherently Fire-Safe Polymers," University of Massachusetts: Ahmerst, Mass., (2000); J. L. Jurs, et al, *SAMPE International Symposium*, 1244 (2000); Lyon, R. In *International Aircraft Fire and Cabin Safety Research Conference*; Atlantic City, N.J., (2001); J. L. Jurs, J. M. Tour, *Polymer*, 44, 3709 (2003)]. When BPC decomposes thermally, it releases HCl gas as well as forming a polycyclic aromatic decomposition product that serves as a char layer. This unique ability to fight the flame front in both the gas phase and condensed phase is helpful in creating materials with excellent fire resistance properties [Lyon, R. In *International Aircraft Fire and Cabin Safety Research Conference*; Atlantic City, N.J., (2001); S. I. Stoliariv, et al, *Polymer*, 43, 5463 (2002)].

Most flame retardant polymers are highly rigid structures containing large amounts of aromatic char-forming functionality. These polymers tend to be hard to process and have high melting temperatures, resulting in elevated cost and rigorous processing requirements. The incorporation of flexible linkers for making processable polymers, an approach commonly used in making vinyl addition polymers, has not been considered a viable approach to making flame retardant polymers since the flexible linkers tend not to be flame resistant. Polymers made using BPC-based chain growth systems, however, could contain both the flexibility of a vinyl backbone and the fire resistance qualities inherent in BPC. Such polymers could overcome the processing difficulties of other BPC polymers, while still retaining their ability to rate as V-0 as tested by UL-94 standards (Underwriters Laboratories).

SUMMARY

The present invention is directed to novel flame retardant monomers and polymers, wherein the flame retardant properties of the polymers are provided by functionality in pendant groups 101 attached to a polymer backbone 102 (see FIG. 1). The present invention is also directed to methods of making such polymers and monomers, and articles of manufacture incorporating such monomers and polymers.

Generally, flame retardant monomers of the present invention comprise a form such as:

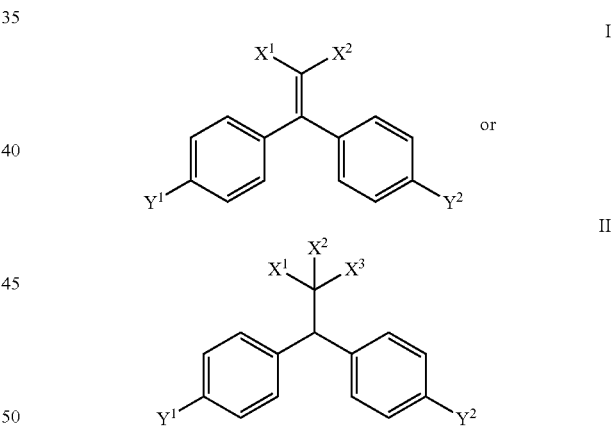

wherein $X^1$, $X^2$, and $X^3$ are each selected from the group consisting of H, Cl, Br, F, I, and combinations thereof, and wherein not all of $X^1$, $X^2$, and $X^3$ are H; wherein $Y^1$ is a polymerizable unit; and wherein $Y^2$ is selected from the group consisting of OH, H, Cl, Br, F, I, another polymerizable unit (for crosslinking), and combinations thereof. Generally, the polymerizable unit comprises a functional moiety selected from the group consisting of an epoxide, an alkene, an alkyne, and combinations thereof. In some embodiments, the polymerizable unit comprises a functional group selected from the group consisting of functional groups 1-11 below. Note that in some embodiments, the polymerizable unit comprises a spacer between the functional group and I or II. Such spacer groups can have the general formula —$[C(Z)_m]_n$—, wherein C is carbon, Z comprises species selected from the group consisting of H, C, O, N, and combinations thereof, m can be either one or two, and n can be zero (i.e., no spacer), or a number greater than or equal to 1.

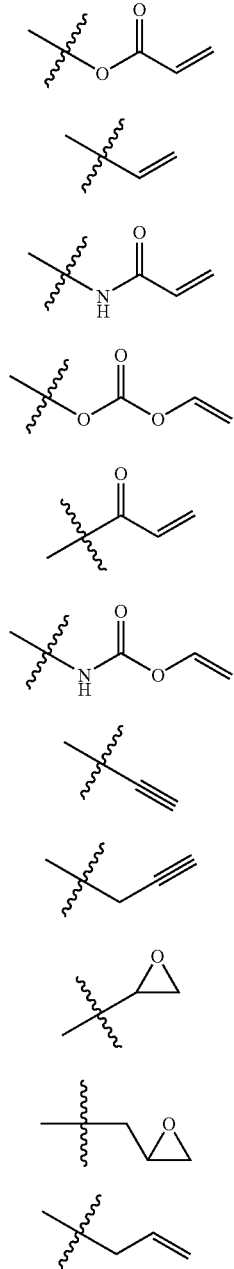

Generally, polymers made from or with any of the above-described monomer comprise pendant groups of the form:

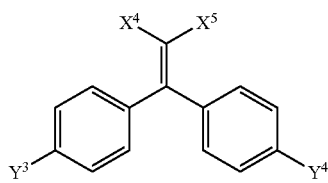
III

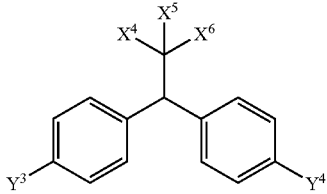
IV wherein the pendants are attached to the polymer backbone through $Y^3$, wherein $Y^4$ is selected from the group consisting of H, OH, Br, Cl, F, I, and combinations thereof; and wherein $X^4$, $X^5$, and $X^6$ are each selected from the group consisting of H, Cl, Br, F, I, and combinations thereof, wherein not all of $X^4$, $X^5$, and $X^6$ are H; and wherein the polymer backbone can be selected from the group consisting of —[CCH]$_n$—, —[CHCH$_2$]$_n$—, and combinations thereof, and any other suitable polymer backbone; and wherein pendant groups are attached through $Y^3$ (i.e., typical vinyl polymers).

Referring to FIG. 2, pendant groups III and/or IV are attached to a polymer backbone such as one of those described above, wherein FIG. 2A depicts a random combination of pendant groups III and IV, and FIG. 2B depicts a scenario in which a flame-retardant pendant group does not emanate from every repeat unit Such polymers are made by the polymerization of one or more variants of the monomers depicted by monomers I and II. Additionally or alternatively, the monomers I and II can be copolymerized with each other, and/or with other monomers having polymerizable groups compatible with monomers I and II. Such copolymers can be products of alternating (e.g., —A—B—A—B—), random or block copolymerization.

Such polymers can be polymerized by a variety of initiators and/or techniques, including, but not limited to, AIBN, di-t-butylperoxide, di-benzoylperoxide, light, heat, cations, anions, catalysts [e.g., metathesis catalysts like Schrock or Grubbs-type catalysts, see Furstner, A. Angew. Chem. Int Ed., 39, 3012-3043 (2000)], and combinations thereof].

In some embodiments, when monomers I and/or II comprise a functional group with two polymerizable units, such as a bis-alkene, the polymer and/or copolymer made with such monomeric species is capable of undergoing crosslinking to form a network structure.

The present invention is also directed to materials and articles of manufacture comprising any of the above-described polymers. Such materials and articles may comprise exclusively the above-described polymeric species, or they may be blended and/or mixed and/or polymerized with other materials to form novel composite or blended materials and articles made with such novel composites or blends. In some embodiments, the other materials are other polymers. In these or other embodiments, the other materials comprise additives such as, but not limited to, anti-drip agents (e.g., TEFLON), metal oxides (e.g., Sb$_2$O$_3$), anti-degradation agents, colorants, carbon-carbon composites, and combinations thereof. It is, however, an advantage of the present invention that "synergists" such as Sb$_2$O$_3$ need not be present to provide flame retardant properties.

In some embodiments, the present invention relates to classes of inherently flame retardant polymers that have been synthesized using vinyl or acroyl bisphenol C monomers. Incorporating these monomers in a chain-growth system can yield high molecular weight materials that are easily processed; unlike the step-growth polymer approaches. Such polymers can be synthesized using vinyl and acrylate addition polymerizations, yielding products that all achieve a V-0 rating using standard UL-94 tests. Along with the V-0 rating, these polymers have total heat release values on the order of 10-12 kJ/g and approximately 20% char formation. With continued heating, such polymers tend to char and not burn. No synergist (e.g., $Sb_2O_3$) was needed, although it could be added, if desired, for further activation. These new inherently flame retardant polymers typically can have molecular weights in the range of about 600,000 to over 1 million Daltons. In some cases, to retard ceiling temperature (depolymerization) upon heating, it may be advantageous to cap the growing polymer chain in the polymerization flask, with an end group that can retard depolymerization, such as iodomethane for an anionic polymerization.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
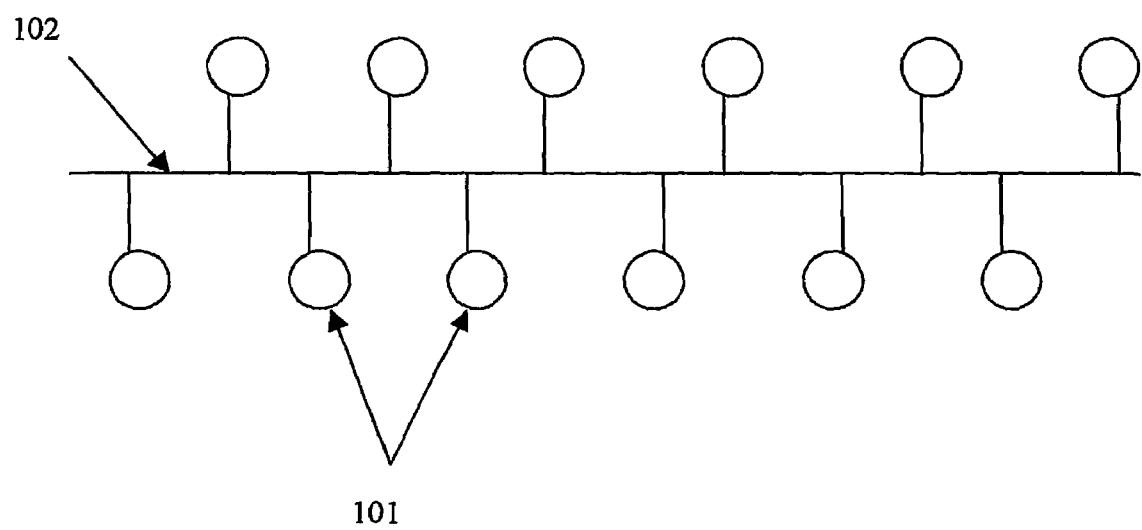
FIG. 1 illustrates a flame retardant polymer comprising a generic backbone 102 attached to which are pendant groups 101, the pendant groups bearing the flame retardant properties.

The present invention is directed to novel flame retardant monomers and polymers, wherein the flame retardant properties of the polymers are provided by functionality in pendant groups attached to a polymer backbone (as opposed to the polymer backbone itself possessing flame retardant properties. The present invention is also directed to methods of making such polymers and monomers, and articles of manufacture incorporating such monomers and polymers. While the making and/or using of various embodiments of the present invention are discussed below, it should be appreciated that the present invention provides many applicable inventive concepts that may be embodied in a variety of specific contexts. The specific embodiments discussed herein are merely illustrative of specific ways to make and/or use the invention and are not intended to delimit the scope of the invention.

Generally, flame retardant monomers of the present invention comprise a form such as:

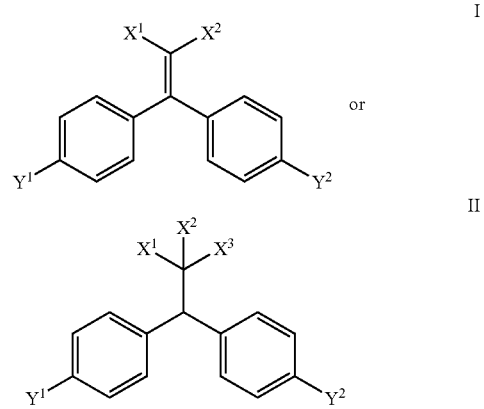

wherein $X^1$, $X^2$, and $X^3$ are each selected from the group consisting of H, Cl, Br, F, I, and combinations thereof, and wherein not all of $X^1$, $X^2$, and $X^3$ are H; wherein one of $Y^1$ is a polymerizable unit; and wherein $Y^2$ is selected from the group consisting of OH, H, Cl, Br, F, I, another polymerizable unit, and combinations thereof. Note, however, that the polymerizable unit need not be located in the para position of the ring on which it resides; it can be located in the ortho and meta positions as well. Generally, the polymerizable unit comprises a functional moiety selected from the group consisting of an epoxide, an alkene, an alkyne, and combinations thereof. In some embodiments, the polymerizable unit comprises a functional group selected from the group consisting of functional groups 1-11 below. This group will herein be referred to as polymerizable moieties 1-11. Note that in some embodiments, the polymerizable unit comprises a spacer between the functional group and I or II. In some embodiments, I is derived from II. Such spacer groups can have the general formula —$[C(Z)_m]_n$—, wherein C is carbon, Z comprises species selected from the group consisting of H, C, O, N, and combinations thereof, m can be either one or two, and n can be zero (i.e., no spacer), or a number greater than or equal to 1.

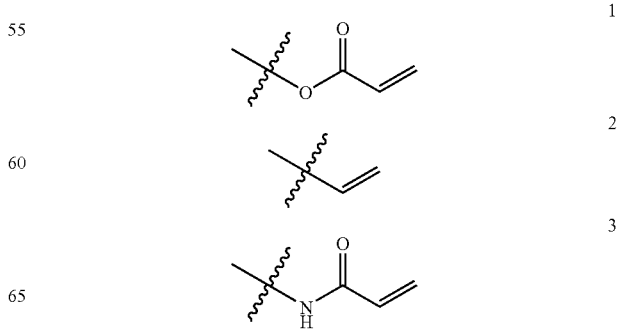

-continued

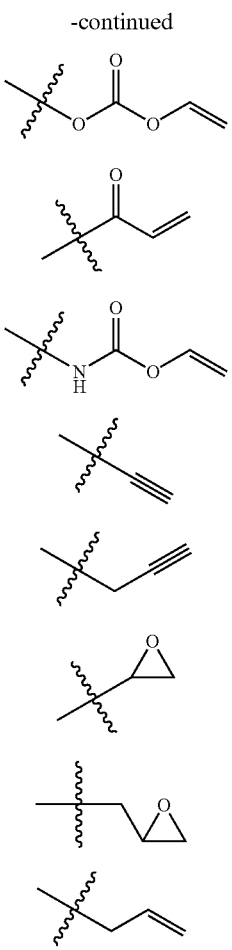

4

5

6

7

8

9

10

11

Generally, polymers made from or with any of the above-described monomers comprise pendant groups of the form:

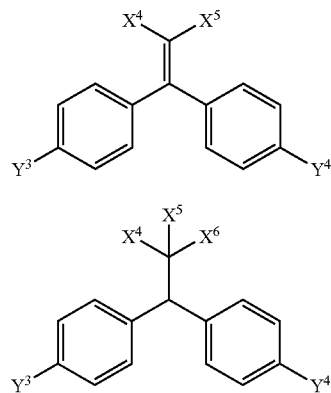

III

IV wherein the pendants are attached to the polymer backbone through $Y^3$, wherein $Y^4$ is selected from the group consisting of H, OH, Br, Cl, F, I, and combinations thereof; and wherein $X^4$, $X^5$, and $X^6$ are each selected from the group consisting of H, Cl, Br, F, I, and combinations thereof, and wherein not all of $X^4$, $X^5$, and $X^6$ are H; and wherein the polymer backbone can be selected from the group consisting of —[CCH]$_n$—, —[CHCH$_2$]$_n$—, and combinations thereof, and any other suitable polymer backbone; and wherein the pendant groups are attached through $Y^3$ (i.e., typical vinyl polymers). Generally, it is desirable that at least one of $X^4$, $X^5$, and $X^6$ (and $X^1$, $X^2$, and $X^3$ above) be Cl or Br.

Figure 2:
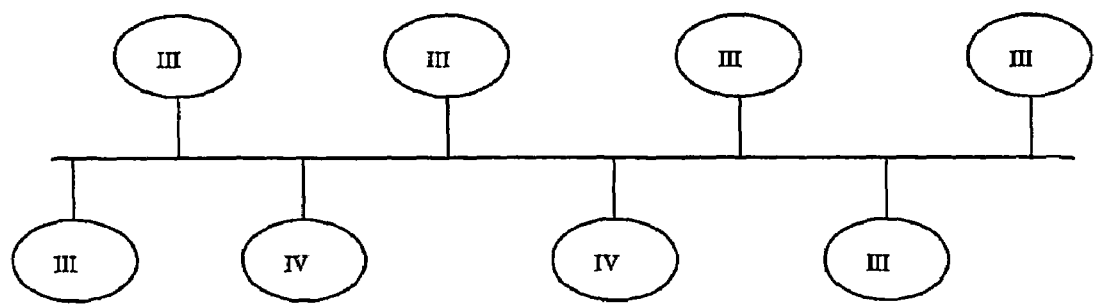
FIG. 2 illustrates a flame retardant polymer wherein the polymer comprises a random combination of pendant groups III and IV (A), and wherein a flame retardant pendant group does not emanate from every repeat unit (B)
Figure 2:
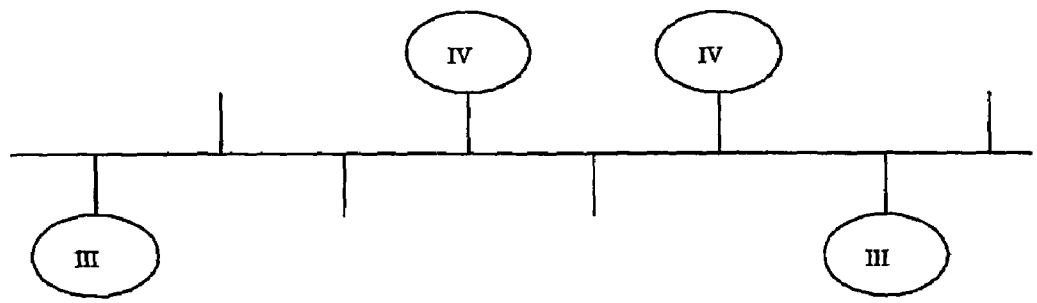

Such polymers vary in the amount of pendant groups III and/or IV which are attached to the polymer backbone. Referring to FIG. 2, pendant groups III and/or IV are attached to a polymer backbone such as one of those described above, wherein FIG. 2A depicts a random combination of pendant groups III and IV, and FIG. 2B depicts a scenario in which a flame-retardant pendant group does not emanate from every repeat unit Such polymers are made by the polymerization of one or more variants of the monomers depicted by monomers I and II. Additionally or alternatively, the monomers I and II can be copolymerized with each other, and/or with other monomers having polymerizable groups compatible with monomers I and II. Such copolymers can be products of alternating (e.g., —A—B—A—B—), random or block copolymerization (e.g., —A—A—B—B—A—A—).

Such polymers can be polymerized by a variety of initiators and/or techniques, including, but not limited to, AIBN, di-t-butylperoxide, di-benzoylperoxide, light, heat, cations, anions, catalysts (e.g., metathesis catalysts like Schrock or Grubbs), and combinations thereof. The processing of similar such species is known and established in the art.

In some embodiments, when monomers I and/or II comprise a functional group with two polymerizable units, such as a bis-alkene or di-vinyl unit, the polymer and/or copolymer made with such monomeric species (i.e., possessing similar such polymerizable units) is capable of undergoing crosslinking with itself or another polymer.

Any of the above-described embodiments can also be carried out using varients of monomers I and II, such as monomers V and VI

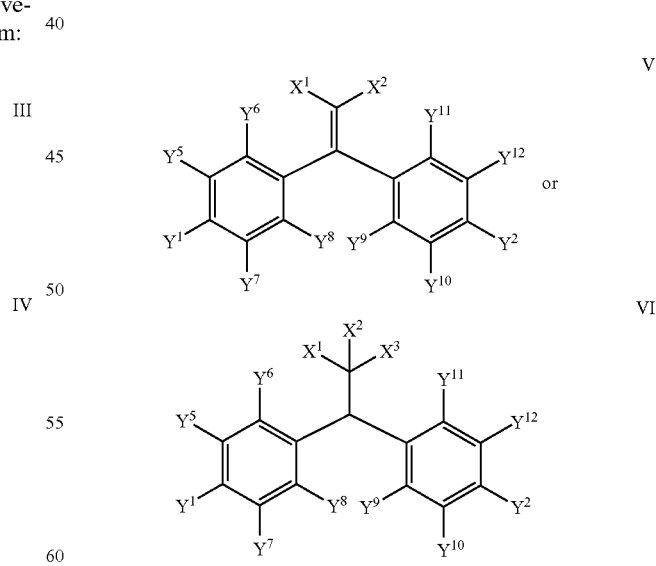

V or

VI

Wherein each of $Y^5$-$Y^{12}$ is selected from the group consisting of H, F, Cl, Br, I and combinations thereof. Moreover, only one of the pendant arm $Y^1$-$Y^2$ and $Y^5$-$Y^{12}$ need bear the polymerizable unit. It need not necessarily bear the polymerizable unit para to the central carbon of V or VI.

As above with monomers I and II, monomers V and VI can be used to form flame retardant polymers comprising pendant groups VII and VIII.

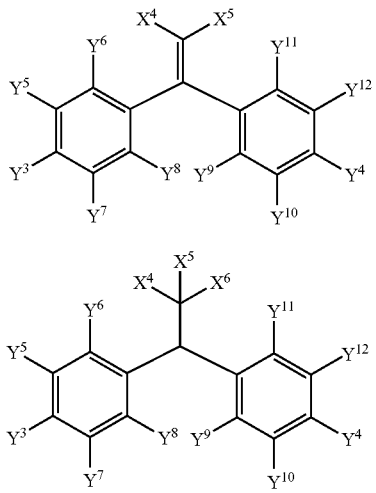

wherein pendant groups VII and VIII are attached to the polymer backbone through $Y^3$, as above for pendant groups III and IV. Moreover, attachment to the polymer backbone need only be through only one of the pendant arm, $Y^3$-$Y^{12}$. It need not necessarily be attached through the unit para to the central carbon of VII or VIII.

The present invention is also directed to materials and articles of manufacture comprising any of the above-described polymers. Such materials and articles may comprise exclusively the above-described polymeric species, or they may be blended and/or mixed with other materials to form novel composite or blended materials and articles made with such novel composites or blends. In some embodiments, the other materials are other polymers. In these or other embodiments, the other materials may comprise additives such as, but not limited to, anti-drip agents (e.g., TEFLON), metal oxides, synergists (e.g., $Sb_2O_3$), anti-degradation agents, colorants, carbon-carbon composites, and combinations thereof.

Due to the excellent flame retardant characteristics of bisphenol C (BPC) and reflective of some embodiments of the present invention, Applicants have made new asymmetric BPC (ABPC) monomers with an easily polymerized acrylate functional group (in this context, the term asymmetric is not used to mean chiral, but rather that the molecule is functionalized asymmetrically—the ends having different functionalities). Acrylic polymers are known for their resistance to heat, sunlight, and weathering—which makes them an excellent candidates for flame retardant polymers [J. R. Stewart, "Synthesis and Characterization of Chlorinated Bisphenol-Based Polymers and Polycarbodiimides as Inherently Fire-Safe Polymers," University of Massachusetts: Ahmerst, Mass., (2000)]. The general approach to making these acrylate polymers was to incorporate the flame retardant BPC as a pendant group extending off the acrylate skeleton. This has produced a flame retardant and processable polymer that can be melted and molded into a new flame resistant material.

In some embodiments, the present invention relates to classes of inherently flame retardant polymers that have been synthesized using vinyl or acroyl bisphenol C monomers (as above). Incorporating these monomers in a chain-growth system yields high molecular weight materials that are easily processed. Such polymers can be synthesized using vinyl and acrylate addition polymerizations, yielding products that achieve V-0 ratings using standard UL-94 tests. Along with the V-0 rating, these polymers have total heat release values on the order of 10-12 kJ/g with approximately 20% char formation. With continued heating, such polymers tend to char and not burn. No synergist (e.g., $Sb_2O_3$) was needed. Typically, to have a halogenated compound be useful as a vapor phase retardant of fire, a synergist must be present. These are often added in ~10 wt % relative to the final weight of the finished polymeric product. Not having to add an additional 10 wt % material is cost effective, and also not having it allows the retention of more of the material's efficacious mechanical properties. These new inherently flame retardant polymers typically can have molecular weights in the range of about 600 k to over 1 million Daltons.

In the above-mentioned embodiments, the present invention relates to polymeric flame retardants derived from a bisphenol C (BPC) analogue unit that has one or more vinyl pendants for effecting a vinyl polymerization, wherein the vinyl group might emanate from the aryl ring or come via an acroyl unit appended to one of the original phenolic groups. Termed a BPC analogue herein, they may or may not bear the original phenolic units. The 1,1-dichloro-2,2-diphenylethene unit (or its precursor, the 1,1,1-trichloro-2,2-diphenylethane) is the critical portion. Note that the chloro units could be substituted with other halogens and the phenyl units could be replaced with other aromatics or substituted benzenes or heterocycles such as thiophenes, pyridines, pyrazine or imidazole rings.

Applicants have developed a novel flame retardant polyacrylate polymer as well as other vinyl polymers with pendant bisphenol C-analogue functionality that is itself highly nonflammable and can be used as the sole component for a plastic or may help to impart flame resistance when blended with a polymer that is normally highly flammable. These new flame retardant polymer can be used "as is" in the blend with no need for the addition of synergists (e.g., $Sb_2O_3$) that are normally used to help impart flame resistance to plastics. As such, the present invention provides for a new polymeric flame retardant polymer, derived from a bisphenol C (BPC) unit that has one or more vinyl pendants for effecting a vinyl polymerization. This could be used as the exclusive monomer in the system or as a co-monomer along with other vinyl monomers. Conversely, the BPC-derived vinyl polymer or co-polymer could be blended with other plastics to afford flame retardancy to the system. The primary difference between this approach and other BPC systems is that the approach described herein uses the BPC as a pendant group in, for example, a vinyl polymerization, thereby permitting the formation of higher molecular weight systems that will lend themselves to both thermoplastics and thermosets (upon addition of a suitable crosslinker). This can be used in conjunction with additives such as, but not limited to, nanoclays, carbon nanotubes, TEFLON, chlorinated polyethylene, or other additives, to impart anti-drip features. Additionally, this pendant moiety could be attached directly to polystyrene and its derivatives using a 2,2,2-trihalo-1-aryl-1-ethanol intermediate in the presence of acid (Lewis or Brönsted) followed by a dehydrohalogenation. The dehydrohalogenation could be effected before polymer deployment or more simply in the fire scenario through in situ thermal elimination.

The present invention has particular application in materials of aircraft construction and componentry. A plastic blend containing the flame retardant polymer could, for example, be molded into panels or structural components to be used in a variety of aircraft applications. These materials have the potential to be used in a variety of other transportation applications (e.g., cars, boats, trains, etc) and other construction applications where plastics are already being used. As existing blends do not perform as well as the blends made with the new flame retardant polymers of the present invention, it is expected that the use of the inventive flame retardant polymer will lower the cost of production of these materials of construction in the transportation industry and will lead to a reduction in the loss of life due to smoke inhalation and fire in accidents, wrecks, crashes, and other mishaps. Materials made with this new flame retardant polymer should have utility in materials of construction in airplanes, trains, buses, trucks, helicopters, and automobiles. It is also anticipated that this material could be used in construction of buildings and homes to impart some protection to residents and occupants in case of a fire, and in the housings of electronic equipment which must be flame retardant to prevent catastrophic fires due to a small short circuit.

Advantages of the present invention over the prior art stem from the fact that existing plastics, and vinyl polymers in particular, can be easy to process and have widespread utility, but are also very flammable; thus they need to be treated with heavy doses of flame retardant additives. In UL 94 test applications, the vinyl-derived polymers of the present invention do not burn. It is not even a matter of their self-extinguishing, but even upon continued application of the flame in the UL 94 test chamber, the polymers do not burn. And achieving high molecular weights coupled with easy processing makes them quite attractive as candidates for flame retardant applications.

In some embodiments, such flame retardant material is made first through the attachment of a vinyl group to the aryl moiety of the system. This can be done through an acroyl group being added to the monomer, or simple a vinyl pendant on the aryl ring of the 1,1-dichloro-2,2-diphenylethene. This can be accomplished in 1-4 synthetic steps for monomer preparation, followed by polymerization. Alternatively, one could functionalize polystyrene directly.

An additional advantage of the inventive polymeric material is that its physical properties can be finely tuned using different monomers in its preparation, or by using additives to achieve the exact characteristics desired. There may be the need for an anti-drip additive in the thermoplastics such as nanoclays, TEFLON, or chlorinated polyethylene. Furthermore, the BPC analogues can be copolymerized with other monomers to help impart greater impact resistance or other desirable features. The polymerization can be effected by several methods as described above.

The following examples are provided to more fully illustrate some of the embodiments of the present invention. It should be appreciated by those of skill in the art that the techniques disclosed in the examples which follow represent techniques discovered by the inventors to function well in the practice of the invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Figure 3:
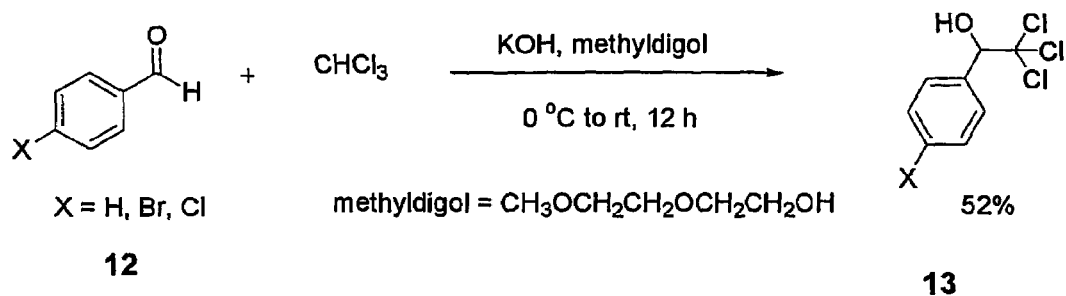
FIG. 3 depicts the synthesis of carbinol 13 from a benzaldehyde 12, in accordance with embodiments of the present invention.

The asymmetric bisphenol C (ABPC) structures of the present invention are made from inexpensive and readily available starting materials (by asymmetric it is meant that the two aryl groups have differing functional moieties). This Example serves to illustrate the first step in this process, i.e., to produce the trichloroethanol product often referred to as the carbinol. Referring to FIG. 3, the carbinol 13 is synthesized by slowly adding (with stirring) a solution of potassium hydroxide and methyldigol (diethylene glycol monomethylether) to a solution of benzaldehyde 12 and chloroform chilled at 0° C. Specifically, the carbinol (2,2,2-trichloro-1-phenyl-ethanol) (13) is prepared by the following method.

To a 250 mL three necked round bottom flask, equipped with a stir bar and addition funnel and purged with nitrogen was added benzaldehyde and chloroform. Potassium hydroxide (1.2 equivalents) (KOH) dissolved in diethylene glycol monomethyl ether (methyldigol) was added dropwise via the addition funnel. The reaction mixture was cooled to 0° C. while the KOH and methyldigol was added slowly over 6 hours. The reaction was then allowed to warm to room temperature with stirring for 12 hours. The reaction was then poured into cold water and diluted with methylene chloride. The two layers were separated and the organic layer was washed with HCl (0.1 N), and $H_2O$ (2×). The organic layer was dried over magnesium and filtered through filter paper. Solvent was removed via rotary evaporation. The final product (13) was isolated via vacuum distillation 85-110° C. (1 atm).

EXAMPLE 2

Figure 4:
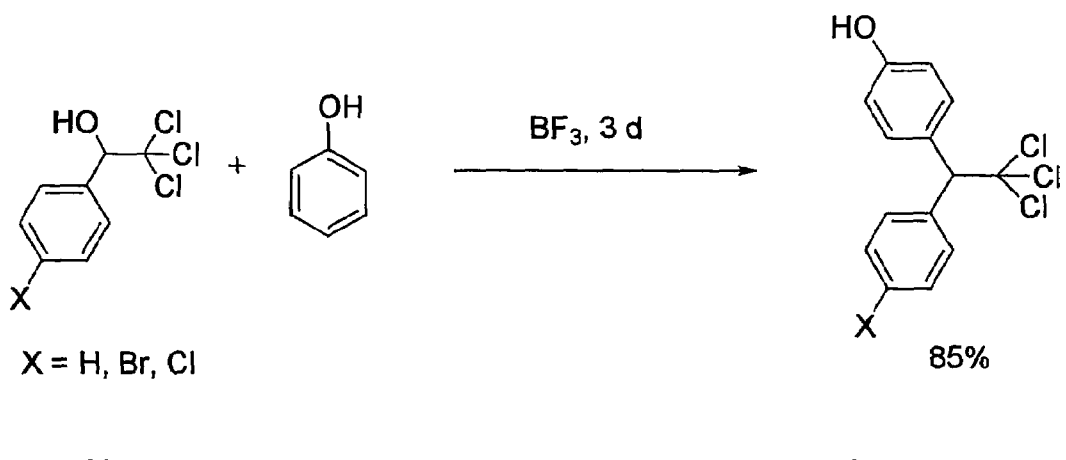
FIG. 4 depicts the reaction of the carbinol 13 with phenol to yield 14, in accordance with embodiments of the present invention.

This Example serves to illustrate how the resulting carbinol 13, purified by vacuum distillation, is reacted with phenol in the presence of $BF_3$ gas over several days to yield the asymmetrical molecule (14), as shown in FIG. 4. This process takes several daily additions of $BF_3$ and mechanical stirring to afford the dark viscous mixture, which is then purified by column chromatography. Specifically, 2-(p-hydroxyphenyl)-2'-(phenyl)-1,1,1-trichloroethane (14) was synthesized by the following process.

To a 100 mL three necked round bottom flask, equipped with a stir bar, mechanical stirrer, and a gas inlet tube was added 13 and phenol (0.98 equivalents), the flask was sealed with a septa and boron trifluoride ($BF_3$) was bubbled into the solution for 20 minutes, with constant stirring. The thick solution was stirred vigorously and $BF_3$ was bubbled into the reaction mixture every 12 hours for 3 to 5 days. The reaction was then poured into cold water and diluted with ethyl acetate. The two layers were separated and the organic layer was washed with $K_2CO_3$ (1 M, 2×) and $H_2O$ (2×). The organic layer was dried over magnesium and filtered through filter paper. Solvent was removed via rotary evaporation. The final product (14) was isolated via column chromatography (9:1; hexane/ethyl acetate).

EXAMPLE 3

Figure 5:
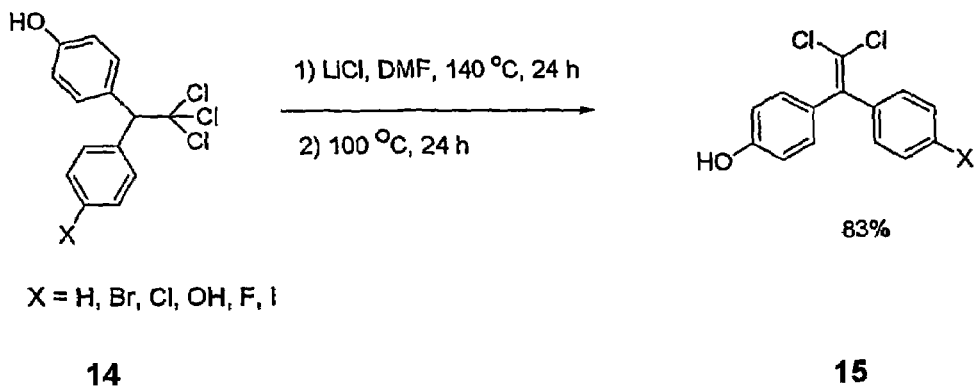
FIG. 5 depicts the dehydrohalogenation of 14 to yield 15, in accordance with embodiments of the present invention.

This Example serves to illustrate the dehydrohalogenation of the ABPC species 14, done using the standard procedure of lithium chloride addition in DMF at 140° C. for 24 hours then slowly decreasing the heat to 100° C., as shown in FIG. 5. Specifically, 2-(p-hydroxyphenyl)-2'-(phenyl)-1,1-dichloroethene (15) was prepared by the following method.

To a 250 mL round bottom flask, equipped with a stir bar and reflux condenser and purged with nitrogen, was added 2-(p-hydroxyphenyl)-2'-(phenyl)-1,1,1-trichloroethane, KOH (7 equivalents), and MeOH (150 mL). The flask was then sealed under nitrogen with a septum and heated to reflux for 24 hours. The reaction mixture was then diluted with ethyl acetate. The organic layer was washed with $H_2O$ (3×) and the aqueous layer was then extracted with ethyl acetate (3×). The organic layers were combined and dried over magnesium sulfate and filtered through filter paper. Solvent was then removed via rotary evaporation and the resulting solid (15) was dried in vacuo for 24 hours.

EXAMPLE 4

Figure 6:
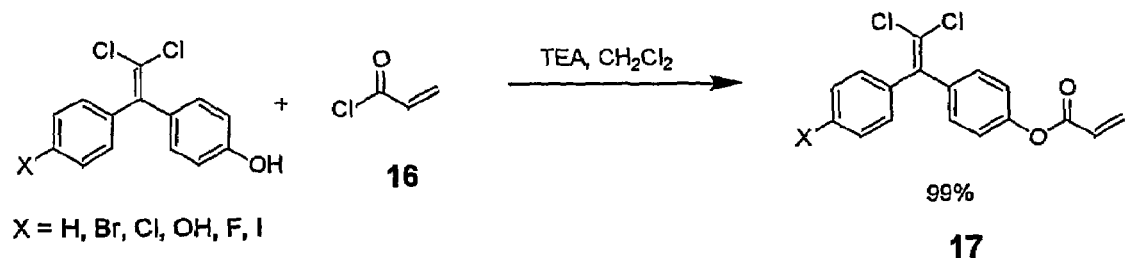
FIG. 6 depicts the reaction of acryloyl chloride with 15 to yield monomer 15, in accordance with embodiments of the present invention.

This Example serves to illustrate the final step in the synthesis of an acrylate monomer 17, this step involving the addition of acryloyl chloride 16 to a solution of the ABPC species 15, triethylamine and in methylene chloride, as shown in FIG. 6. Specifically, acrylic acid [2-(p-hydroxyphenyl)-2'-(phenyl)-1,1-dichloroethene] ester (17) was prepared by the following method.

To a 100 mL round bottom flask equipped with a stir bar and purged with nitrogen was added the acrylate monomer 15. The reaction flask was evacuated and backfilled with nitrogen (3×). Methylene chloride and triethylamine (1.5 equivalents) where added to the flask via syringe and cooled on an ice bath. Acryloyl chloride 16 (1.1 equivalents) was slowly added dropwise via syringe. The ice bath was removed and the resulting solution was allowed to warm to room temperature and stirred for 12 hours. The reaction was then quenched by opening the flask to air, and the reaction mixture was rotary evaporated to dryness. The final product (17) was isolated via column chromatography (9:1; Hexane/Ethyl acetate).

EXAMPLE 5

Figure 7:
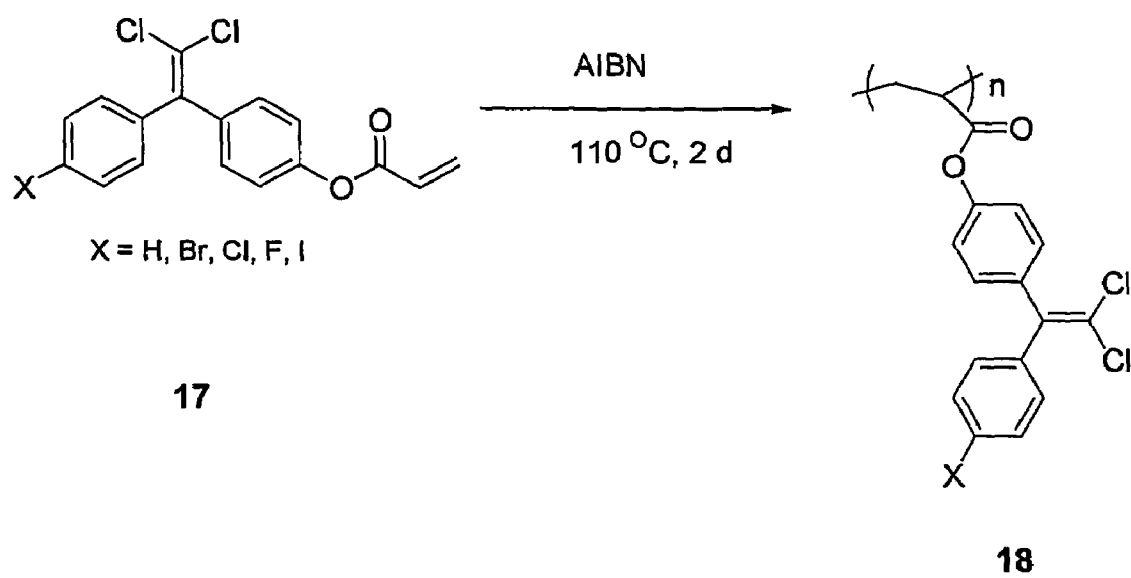
FIG. 7 depicts the polymerization of monomer 17 to yield polymer 18, in accordance with embodiments of the present invention.

This Example serves to illustrate how an acrylate polymer 18 is made by a bulk polymerization of 17 with 2,2'-azobisisobutyronitrile (AIBN) at 110° C. for 2 days, as shown in FIG. 7. Specifically, Polyacrylate A (18) was prepared by the following method.

To a 100 mL round bottom flask equipped with a stir bar was added the acrylate monomer 17 (note that if X=OH, another polymerization protocol would be needed since phenolic-OH is a radical chain inhibitor) and 2,2'-azobisisobutyronitrile (AIBN: 1000/1; monomer/initiator) and sealed with a septa under nitrogen. The reaction flask was evacuated and backfilled with nitrogen (3×). The reaction mixture was then placed in an oil bath at 110° C. and stirred for 2 days. The reaction was then cooled to room temperature, dissolved in chloroform and precipitated in methanol. (X=H) $M_w$: 607,300; $M_n$: 321,200. (X=Cl) $M_w$: 280,600; $M_n$: 110,000 (determined by size-exclusion chromatography using polystyrene standards).

Preliminary burn methods conclude this polymer (18 where X=H) works well as a flame resistant material. The polymer dripped, but did not ignite the cotton when it subjected to the HVUL-94 flame test. With the addition of the anti-drip additive, 1 wt % PTFE, the sample did not drip at all. The polymer is considered to be a V-0 material according to the UL-94 test for flammability of plastic materials.

In addition to the above mentioned vinyl polymers, shown below are vinyl monomers 19-24 that could be made using this ABPC core

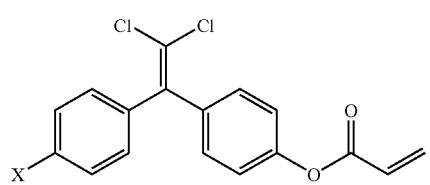

19

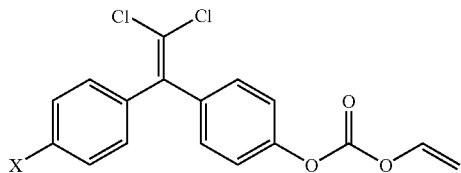

20

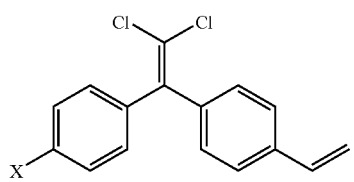

21

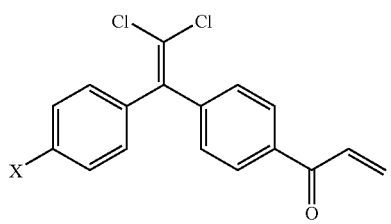

22

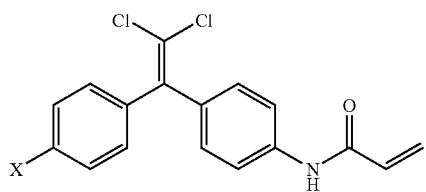

23

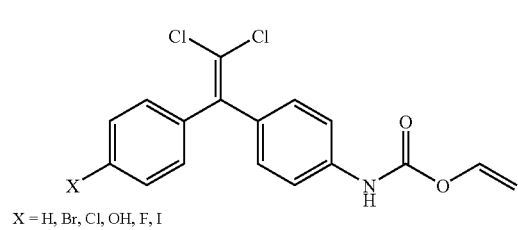

24

X = H, Br, Cl, OH, F, I

EXAMPLE 6

Figure 8:
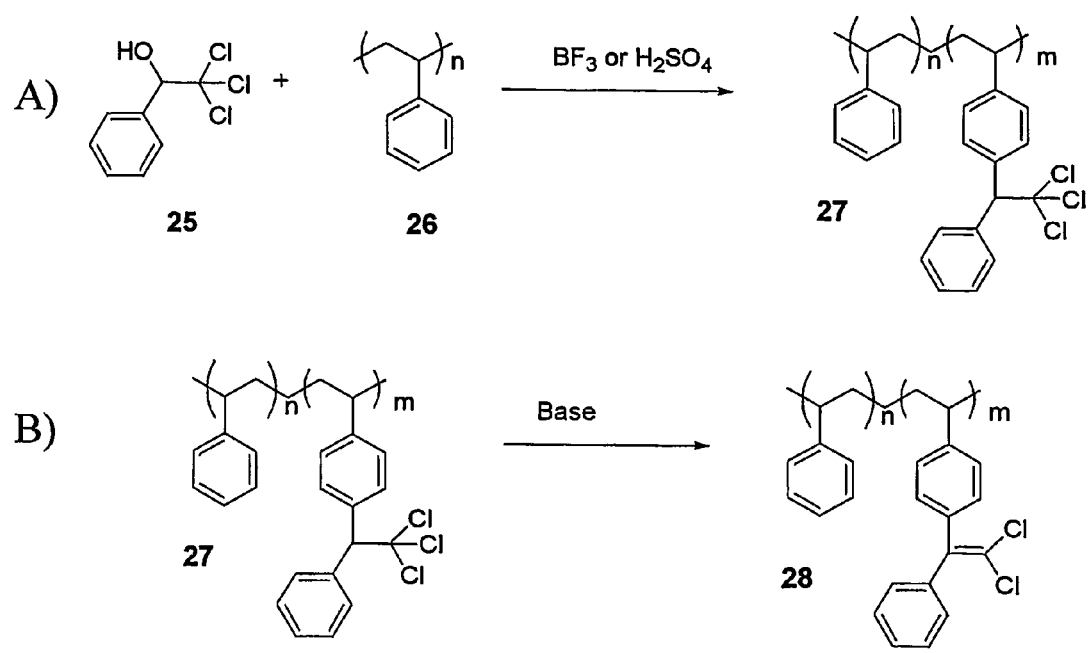
FIG. 8 depicts the reaction of carbinol 25 with polystyrene to yield 27 (A), and the dehydrohalogenation of 27 to yield 28 (B), in accordance with embodiments of the present invention.

Another potential use for the carbinol is to impart flame retardancy to flammable polymers such as polystyrene. By taking a carbinol 25 (13, where X=H) and reacting with polystyrene 26 in the presence of $BF_3$ or sulfuric acid to yield 27, followed by a dehydrohalogenation reaction with base should give the more stable flame retardant polymer 28, as shown in FIG. 8. Polymers 27 and 28 will be referred to herein as polymer structures 27 and 28.

EXAMPLE 7

This Example serves to illustrate UL-94 burn results for the polymer produced in Example 5.

TABLE 1

Burn Results for 18

| Additive | First Ignition[a] (sec) | Observed Dripping[b] | Second Ignition[a] (sec) | Observed Dripping[b] | UL-94 Rating |
|---|---|---|---|---|---|
| Polyacrylate A | 0, 0 | No, No | 1, 1 | No, Yes | V-0, V-0 |
| Polyacrylate A, 1 wt % PTFE | 0, 0 | No, No | 0, 0 | No, No | V-0, V-0 |

[a]Time to self-extinguish after ignition. The two numbers are for two separate tests on two separate samples.
[b]Indicates that molten polymer did (Yes) or did not (No) drip on to cotton patch underneath ignited bar during UL-94 test.
[c]Preliminary tests were performed on smaller samples than dictated by UL-94 standards.
[d]The dripping did not ignite the cotton.

EXAMPLE 8

This Example serves to illustrate additional polymers that can be synthesized and their corresponding UL-94 burn results. Additional polymers were made as below.

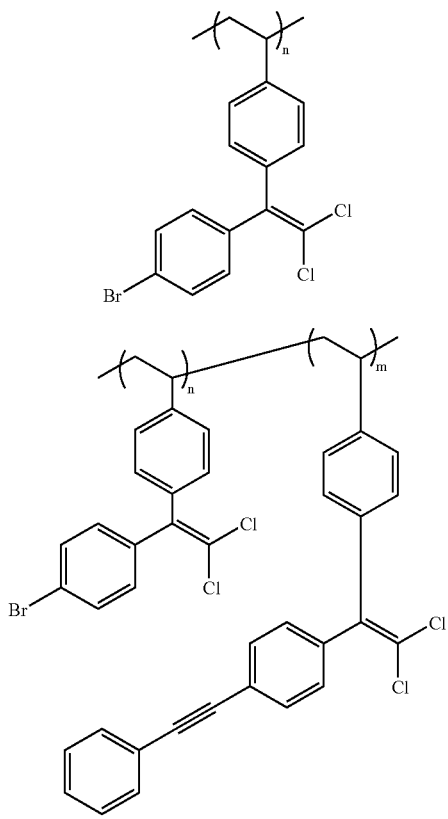

The testing of novel vinyl and acroyl BPC polymers 29 and 30 for flame retardancy was accomplished using the modified UL-94 flame test described above. Polymers 29 and 30 will be referred to herein as polymer structures 29 and 30. Using UL-94 standards to determine whether or not the polymers achieved a V-0 rating, the polymers must self-extinguish the flame within 10 seconds of having the ignition source removed, and this should be maintained during two sequential ignitions. Dripping of the ignited plastic onto a cotton patch is permitted considering no ignition of the cotton occurs. For polymers 29 and 30, sufficient material was not available to blend complete bars, so small 300 mg samples were used for preliminary testing. The results from these tests are listed in Table 2.

TGA (thermal gravimetric analysis) data was collected on each polymer to determine the amount of char each polymer would create after complete combustion. Char % was deduced by allowing several mg of polymer to burn in air on heating in the TGA to 700° C., assuming the amount of material remaining was the char. Polymer 29 had char of 20%; however, after adding phenylacetylene groups to polymer 29 (as seen in polymer 30) the polymer char increased to 50%.

Number average and weight average molecular weights were determined for each polymer using Polymer Labs GPC-220 High Temperature Chromatograph. The glass transition temperatures (Tg) were determined using TA Instruments DSC Q10. Polymer 28 had $M_w$ 862,000 and $M_n$ 560,000 with a $T_g$ of 110° C., while polymer 29 had $M_w$ 1,410,000 and $M_n$ 654,000 with a $T_g$ of 110° C.

TABLE 2

Results of UL-94 flame tests

| Polymer | First Ignition[a] (s) | Observed Dripping[b] | Second Ignition[a] (s) | Observed Dripping[b] | UL-94 Rating |
|---|---|---|---|---|---|
| Polystyrene 28 | 0[c] | No[c] | 0[c] | No[c] | V-0[c] |
| Polystyrene 29 | 0[c] | No[c] | 1[c] | No[c] | V-0[c] |

[a]Time to self-extinguish after ignition. The two numbers are for two separate tests on two separate samples.
[b]Indicates that molten polymer did (Yes) or did not (No) drip on to cotton patch underneath ignited bar during UL-94 test.
[c]Preliminary tests were performed on smaller samples than dictated by UL-94 standards.
[d]The dripping did not ignite the cotton.

In conclusion, Examples 1-8 demonstrate the formation of new vinyl and acroyl BPC monomers that are used to create processible flame retardant polymers in accordance with the present invention. These monomers can be used as the exclusive monomer in a system, or as a co-monomer along with other vinyl monomers, such as other BPC derivatives, or vinyl monomers. The two types of vinyl monomers made here are acrylate and styrene derivatives. Acrylate polymers are known for their resistance to heat, sunlight, and weathering properties, which make them excellent candidates for flame retardant polymers, and styrene polymers are one of the most widely used plastics having applications in almost every industry. Each of the polymers underwent and passed (some preliminary), the UL-94 standards for having a V-0 rating.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A monomer having a form selected from the group consisting of:

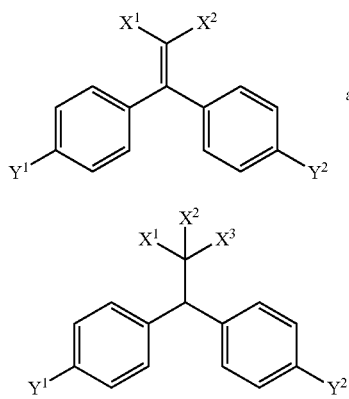

wherein $X^1$, $X^2$, and $X^3$ are each selected from the group consisting of H, Cl, Br, F, I, and combinations thereof;
wherein at least one of $X^1$ and $X^2$ is not H; and
wherein at least one of $X^1$, $X^2$, and $X^3$ is not H;
wherein $Y^1$ is a polymerizable unit;
wherein the polymerizable unit comprises a functional moiety selected from the group consisting of an epoxide, an alkene, an alkyne and combinations thereof; and
wherein $Y^2$ is selected from the group consisting of OH; H; Cl; Br; I; F; $OR^1$, wherein $R^1$ is selected from the group consisting of alkyl, aryl, and combinations thereof; and $R^2$, wherein $R^2$ is selected from the group consisting of alkyl, alkenyl, alkynyl, and combinations thereof.

2. The monomer of claim 1, wherein the polymerizable unit comprises an alkene.

3. The monomer of claim 1, wherein the polymerizable unit is attached to the monomer via a spacer group.

4. The monomer of claim 1, wherein the polymerizable unit is selected from the group consisting of:

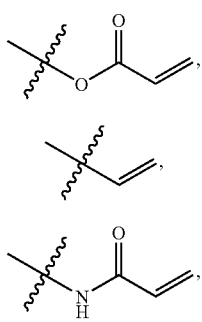

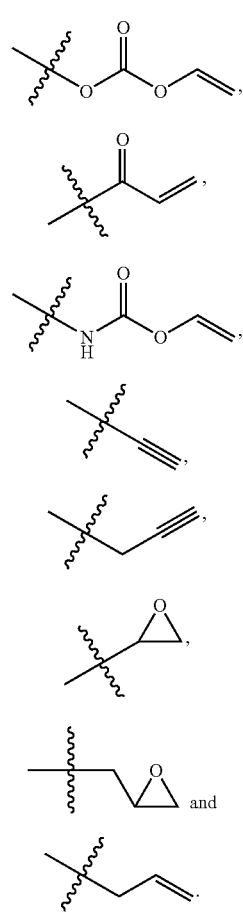

5. The monomer of claim 1, wherein $Y^2$ is selected from the group consisting of OH, H, Cl, Br, I, and F.

6. A monomer having a form selected from the group consisting of:

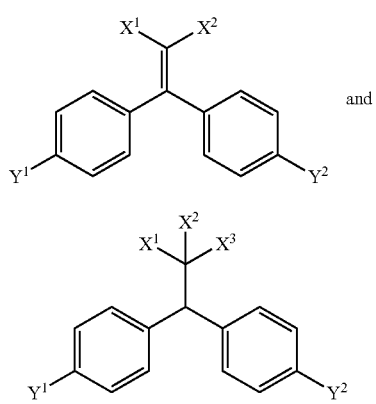

wherein $X^1$, $X^2$, and $X^3$ are each selected from the group consisting of H, Cl, Br, F, I, and combinations thereof;
wherein at least one of $X^1$ and $X^2$ is not H; and
wherein at least one of $X^1$, $X^2$, and $X^3$ is not H;
wherein $Y^1$ is a polymerizable unit comprising at least two polymerizable functional moieties; and wherein $Y^2$ is selected from the group consisting of OH; H; C; Br; I; F; $OR^3$, wherein $R^3$ is selected from the group consisting of alkyl, aryl, alkenyl and combinations thereof; and $R^4$, wherein $R^4$ is selected from the group consisting of alkyl, alkenyl, alkynyl, and combinations thereof.

7. The monomer of claim 6, wherein the polymerizable unit is a bis-alkene.

8. A monomer having a form selected from the group consisting of:

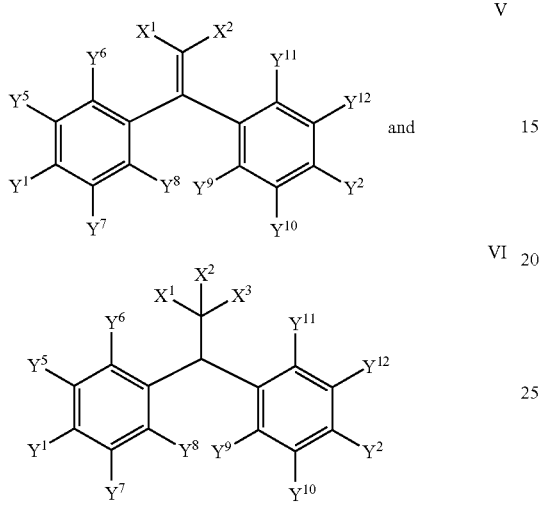

wherein,
a) $X^1$-$X^3$ are each selected from the group consisting of H, Cl, Br, F, I, and combinations thereof;
   wherein at least one of $X^1$ and $X^2$ is not H; and
   wherein at least one of $X^1$, $X^2$, and $X^3$ is not H;
b) at least one of $Y^2$ and $Y^9$-$Y^{12}$ is selected from the group consisting of (i) OH; (ii) H; (iii) Cl; (iv) Br; (v) I; (vi) F; (vii) $OR^5$, wherein $R^5$ is selected from the group consisting of alkyl, aryl, and combinations thereof; (viii) $R^6$, wherein $R^6$ is selected from the group consisting of alkyl, alkenyl, alkynyl, and combinations thereof and (ix) combinations thereof;
c) the remainder of $Y^2$ and $Y^9$-$Y^{12}$ are each selected from the group consisting of H, Cl, Br, F, I, and combinations thereof;
d) at least one of $Y^1$ and $Y^5$-$Y^8$ is a polymerizable unit;
   wherein the polymerizable unit comprises a functional moiety selected from the group consisting of an epoxide, an alkene, an alkyne and combinations thereof; and
e) the remainder of $Y^1$ and $Y^5$-$Y^8$ are each selected from the group consisting of H, Cl, Br, F, I, and combinations thereof.

9. The monomer of claim 8, wherein exactly one of $Y^1$ and $Y^5$-$Y^8$ is a polymerizable unit.

10. The monomer of claim 8, wherein,
(a) $Y^5$-$Y^{12}$ are each selected from the group consisting of H, Cl, Br, F, I, and combinations thereof;
(b) $Y^2$ is selected from the group consisting of (i) OH; (ii) H; (iii) Cl; (iv) Br; (v) I; (vi) F; (vii) $OR^5$, wherein $R^5$ is selected from the group consisting of alkyl, aryl, and combinations thereof; and (viii) $R^6$, wherein $R^6$ is selected from the group consisting of alkyl, alkenyl, alkynyl, and combinations thereof; and
(c) $Y^1$ is a polymerizable unit.

11. The monomer of claim 9, wherein exactly one of $Y^2$ and $Y^9$-$Y^{12}$ is selected from the group consisting of (i) OH; (ii) $OR^5$, wherein $R^5$ is selected from the group consisting of alkyl, aryl, and combinations thereof; and (iii) $R^6$, wherein $R^6$ is selected from the group consisting of alkyl, alkenyl, alkynyl, and combinations thereof.

12. The monomer of claim 9, wherein $Y^2$ and $Y^9$-$Y^{12}$ are each selected from the group consisting of H, Cl, Br, F, I, and combinations thereof.

13. The monomer of claim 9, wherein the polymerizable unit is selected from the group consisting of:

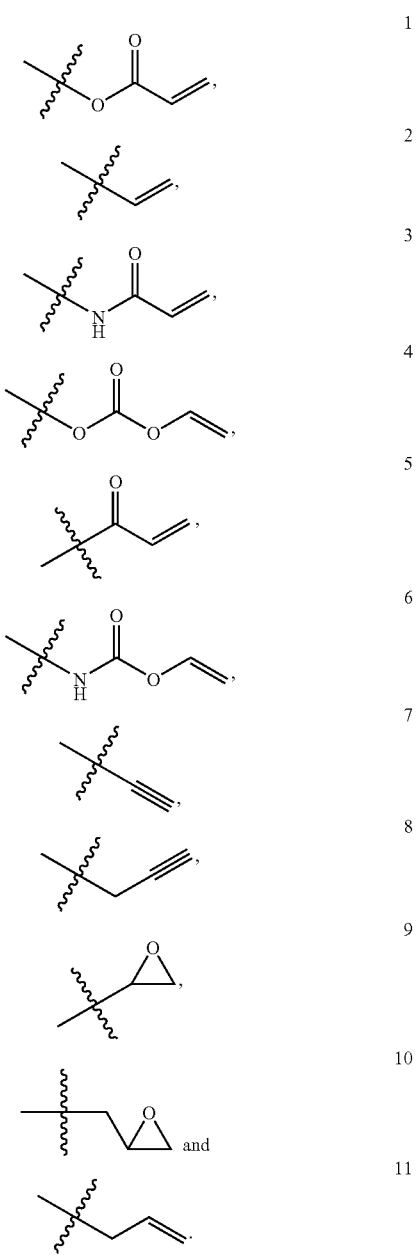

14. The monomer of claim 9, wherein at least two of $Y^2$ and $Y^9$-$Y^{12}$ are selected from the group consisting of (i) OH; (ii) $OR^5$, wherein $R^5$ is selected from the group consisting of alkyl, aryl, and combinations thereof; and (iii) $R^6$, wherein $R^6$ is selected from the group consisting of alkyl, alkenyl, alkynyl, and combinations thereof.

* * * * *

UNITED STATES PATENT AND TRADEMARK OFFICE
CERTIFICATE OF CORRECTION

PATENT NO. : 7,625,988 B2  
APPLICATION NO. : 10/560291  
DATED : December 1, 2009  
INVENTOR(S) : Tour et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1023 days.

Signed and Sealed this

Twenty-first Day of December, 2010

David J. Kappos
*Director of the United States Patent and Trademark Office*